US00RE39862E

(19) United States
(12) Reissued Patent
Ring et al.

(10) Patent Number: US RE39,862 E
(45) Date of Reissued Patent: Sep. 25, 2007

(54) UNSATURATED 14, 15-CYCLOPROPANOANDROSTANES, A METHOD FOR THEIR PRODUCTION AND PHARMACEUTICAL COMPOSITIONS CONTAINING THESE COMPOUNDS

(75) Inventors: Sven Ring, Jena (DE); Walter Elger, Berlin (DE); Guenter Kaufmann, Jena (DE)

(73) Assignee: Schering AG, Berlin (DE)

(21) Appl. No.: 11/008,758

(22) PCT Filed: Nov. 21, 2000

(86) PCT No.: PCT/EP00/11557

§ 371 (c)(1),
(2), (4) Date: May 24, 2002

(87) PCT Pub. No.: WO01/42275

PCT Pub. Date: Jun. 14, 2001

Related U.S. Patent Documents

Reissue of:
(64) Patent No.: 6,710,039
Issued: Mar. 23, 2004
Appl. No.: 10/148,157
Filed: May 24, 2002

(51) Int. Cl.
*A61K 31/56* (2006.01)
*C07J 53/00* (2006.01)

(52) U.S. Cl. ..... 514/178; 552/510
(58) Field of Classification Search ..... 514/178; 552/510
See application file for complete search history.

(56) References Cited

U.S. PATENT DOCUMENTS 2,895,969 A * 7/1959 Batres et al. ..... 552/603
3,201,427 A * 8/1965 Gomarasca et al. ..... 552/620
3,239,512 A * 3/1966 Cross ..... 540/119

FOREIGN PATENT DOCUMENTS

CH 376097 A * 3/1964
DE 31269 A * 1/1961
DE 33136 A * 11/1964
DE 19827523 A1 * 12/1999
EP 0768316 A * 4/1997
GB 839908 A * 6/1960
GB 855800 A * 12/1960
GB 874572 A * 8/1961
GB 928714 A * 6/1963
WO WO-99/67275 * 12/1999
WO WO 99/67275 A * 12/1999

OTHER PUBLICATIONS

P.S. Furth et al., J. Enzyme Inhibition, 1990, vol. 4, pp. 131–135.*
X.S. Fei et al., J. Chem. Soc. Perkin Trans. 1, 1998, pp. 1139–1142.*
Blackmore Peter et al., Molecular Pharmacology, BD. 49, NR. 4, 1996, pp. 727–739.*
R. Ernst: "Dictionary of Engineering and Technology", Vol. 1, Fifth Edition, P. 841.
CRC Hand Book of Chemistry and Physics by D.R. Lide. Boca Raton, Ann Arbor, London, Tokyo, pp. 2–23–2–24.

* cited by examiner

*Primary Examiner*—Barbara P. Badio
(74) *Attorney, Agent, or Firm*—Michael J. Striker

(57) ABSTRACT

The invention relates to new unsaturated 14,15-cyclopropano-androstanes of the general formula (I)

(I)

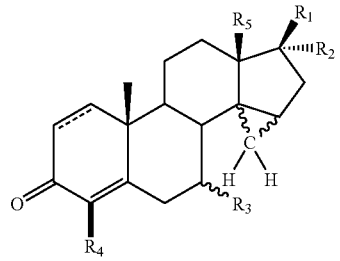

to their synthesis and to pharmaceutical compositions, containing these compounds.

The compounds of formula (I) have gestagenic and/or androgenic activity.

20 Claims, No Drawings

UNSATURATED 14, 15-CYCLOPROPANOANDROSTANES, A METHOD FOR THEIR PRODUCTION AND PHARMACEUTICAL COMPOSITIONS CONTAINING THESE COMPOUNDS

Matter enclosed in heavy brackets [ ] appears in the original patent but forms no part of this reissue specification; matter printed in italics indicates the additions made by reissue.

[This application is a 371 of PCT/EP00/11557 filed Nov. 21, 2000.] *The invention described and claimed hereinbelow is also described in PCT International Patent Application PCT/EP 00/11557, filed on Nov. 21, 2000, which provides the basis for a claim of priority of invention for the claims appended hereinbelow under 35 U.S.C. 365.*

The invention relates to new unsaturated [14,15-cyclopropane-androstanes] *14,15-cyclopropanoandrostanes*, a method for their production and pharmaceutical compositions containing these compounds. Unsaturated [14,15-cyclopropane-androstanes] *14,15-cyclopropanoandrostanes* of the following formula:

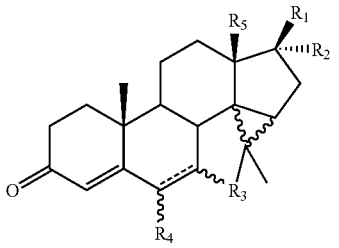

are described in the German [application] *Patent Application* No. 198 27 523.4 (PCT/DE99/01794), which claims a priority earlier than that of the present application, but was published after the latter was filed.

In the formula, $R_1$ is a hydrogen atom, a hydroxy group, an alkyloxy *group*, *an* acyloxy *group*, [alryloxy] *an aryloxy group,* [or] *an* alkylaryloxy group, an —$OCONHR_9$ , or —$OCOOR_9$ group, in which $R_9$ represents a hydrogen atom, an alkyl *group*, *an* aryl *group*, *an* aralkyl *group,* or alkylaryl group with, in each case, 1 to 10 carbon atoms[.];

$R_2$ represents a hydrogen atom, a hydroxyl group, an alkyl *group*, *an* acyl *group*, *an* aryl *group*, *an* aralkyl *group*, or *an* alkylaryl group with, in each case, 1 to 10 carbon atoms[.];

a —$(CH_2)_nCH_2Y$ group, with n=0, 1, or 2, in which Y represents a fluorine *atom*, *a* chlorine *atom*, *a* bromine [or] *atom, an* iodine atom, a cyano *group*, [azide or rhodanide] *an azido group, a thiocyanato* group, an —$OR_{10}$ *group* or *a* —$SR_{10}$ group[.] in which $R_{10}$ represents a hydrogen atom, an alkyl *group*, *an* aryl *group*, *an* aralkyl *group,* or *an* alkylaryl [groups] *group* with, in each case, 1 to 10 carbon atoms or a $COR_9$ acyl group in which $R_9$ represents an alkyl *group*, *an* aryl *group*, *an* aralkyl *group,* or *an* alkylaryl group with, in each case, 1 to 10 carbon atoms, *or* a —$OR_9$[.] *group* in which $R_9$ represents a hydrogen atom, an alkyl *group*, *an* aryl *group*, *an* aralkyl *group,* or *an* alkylaryl group with, in each case, 1 to 10 carbon atoms[.];

a —$(CH_2)_m$—CH═CH$(CH_2)_n$—$R_8$ group in which m=0, 1, 2, or 3 and n=0, 1, or 2 and $R_8$ represents a hydrogen atom[or], an alkyl *group*, *an* aryl *group*, *an* aralkyl *group,* or *an alkylaryl* group with, in each case, 1 to 10 carbon atoms[or], a hydroxyl group, *or* an alkoxy group or an acyloxy group with, in each case, 1 to 10 carbon atoms[.];

[a —$(CH_2)_oC$═$CR_{11}$ group] *a* —$(CH_2)_oC$≡$CR_{11}$ *group* in which o=0, 1, or 2 and $R_{11}$ represents a hydrogen atom, a fluorine *atom*, *a* chlorine *atom*, *a* bromine [or] *atom, an* iodine atom, or an alkyl *group*, *an* aryl *group*, *an* aralkyl *group,* or *an alkylaryl* group with, in each case, 1 to 10 carbon atoms[.]; *or*

$R_1$ and $R_2$ independently of one another represent a keto, methylene, or difluoromethylene group[.];

[there possibly being] *optionally* a double bond *is present* between C-6 and C-7,

[if there is] an α or β cyclopropane group X *is present* between C-14 and C-15, *with* X representing a $CZ_2$ in which Z represents a hydrogen, *a* fluorine *atom*, *a* chlorine *atom*, *a* bromine *atom,* or *an* iodine atom, $R_3$ and $R_4$ independently of one another represent a hydrogen atom[.] *or* an α or β alkyl group with 1 to 10 carbon atoms, and $R_5$ represents an alkyl group with 1 to 3 carbon atoms.

From the EP 0 768 316 A1, steroids are known with [at 14,15 methylene] *at 14,15-methylene* group, which have progesterone activity and, with that, in combination with at least one suitable estrogen, are suitable for hormonal contraception and menopausal hormone replacement therapy (HRT) as well as for the treatment of endometriosis [and] *or* gestagen-dependent tumors.

With this state of the art as background, it is an object of the present invention to prepare new, unsaturated, 14,15-cyclopropano-androstanes.

The objective was accomplished by unsaturated 14,15-cyclopropano-androstanes of the general formula (I):

(I)

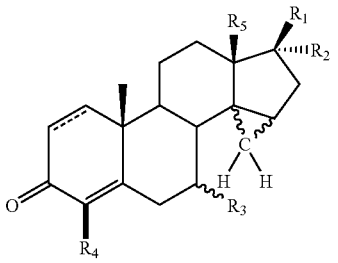

in which $R_1$ represents a hydrogen atom, a hydroxy group, a $C_{1-10}$ alkyl *group*, a $C_{1-10}$ alkyloxy *group*, a $C_{1-15}$ acyloxy *group*, a $C_{4-15}$ aryloxy *group*, a $C_{7-15}$ aralkyloxy *group*, or a $C_{7-15}$ alkylaryloxy group[, in which];

$R_2$ represents a hydrogen atom, a hydroxy group, a $C_{1-10}$ alkyl *group*, a $C_{1-10}$ acyl *group*, a $C_{1-10}$ acyloxy *group*, a $C_{6-15}$ aryl *group*, a $C_{7-15}$ aralkyl *group,* or a $C_{7-15}$ alkylaryl group;

a —$(CH_2)_nCH_2Y$ group, in which n=0, 1, or 2 and Y represents a halogen atom, especially a fluorine, chlorine, bromine, or iodine atom, *or* a pseudohalogen, especially a cyano, [azide or rhodanide] *an azido, or a thiocyanato* group[.];

a —$(CH_2)_m$—CH═CH$(CH_2)_p$—$R_6$ group in which m=0, 1, 2, or 3 and p=0, 1, or 2 and $R_6$ represents a hydrogen atom, a $C_{1-10}$ alkyl *group*, a $C_{6-15}$ aryl *group*, a $C_{7-15}$ aralkyl [or] *group,* a $C_{7-15}$ alkylaryl group[or], a hydroxyl group, a $C_{1-10}$ alkyloxy group, or a $C_{1-10}$ acyloxy group[.];

*a* —$(CH_2)_oC$≡$CR_7$ *group* in which o[–]=0, 1 or 2 and [R7] $R_7$ represents a hydrogen atom, a halogen atom, especially a fluorine, chlorine, bromine, or iodine atom, a $C_{1-10}$ alkyl *group*, a $C_{6-15}$ aryl *group*, a $C_{7-15}$ aralkyl *group*, a $C_{7-15}$ alkylaryl *group,* or a $C_{1-10}$ acyl group[,]*; or*

$R_1$ and $R_2$ together represent a keto *group*, *a* methylene [or] *group, a* difluoromethylene group, or, with inclusion of *a* C-17, form a spirooxirane or a 2,2-dimethyl-1,3-dioxolane[, there being a double bond between C-1 and C-2, there being]; an α or β cyclopropane group *is present* between C-14 and C-15[,]*;*

$R_3$ represents a hydrogen atom or an α or β $C_{1-10}$ alkyl group[,]*;*

$R_4$ represents *a hydroxyl group, a perfluoroalkyl group,* a halogen atom, especially a fluorine atom, a chlorine atom, or *a* bromine atom, or a pseudohalogen, especially [a rhodanide or an azide group, or a hydroxyl or perfluoroalkyl group and] *an azido group or a thiocyanato group;*

$R_5$ represents a $C_{1-4}$ alkyl group[,]*; and*

*optionally a double bond is present between C-1 and C-2;* with the proviso that, if [there is a] *the* double bond *is present* in the 1,2 position, $R_4$, in addition to the meanings given above, may be a hydrogen atom[, as well as their pharmaceutically tolerated salts]*; or*

*pharmaceutically tolerated salts thereof.*

Surprisingly, it was found that the inventive, unsaturated [14,15-cyclopropane-androstanes] *14,15-cyclopropanoandrostanes* of the general formula (I) are compounds with gestagenic and/or androgenic activity.

Within the sense of the invention, pharmaceutically tolerated salts are alkali or alkaline earth salts, especially sodium, potassium or ammonium salts. These salts can be synthesized by standard techniques and methods, which are well known in the art.

Within the sense of the present invention, a "$C_{1-4}$ or $C_{1-10}$ alkyl group" is understood to be a branched or linear alkyl group with 1 to 4 or 1 to 10 carbon atoms. As examples, a methyl, ethyl, n-propyl, i-propyl, n-butyl, i-butyl or t-butyl, n-pentyl, i-pentyl, n-hexyl, 2-methylpentyl, 3-methylpentyl, 2,2-dimethylbutyl or 2,3-dimethylbutyl group are mentioned.

Within the sense of the present application, the concept of "$C_{1-10}$ alkoxy group" is understood to include cyclic or acyclic groups, the alkyl portion of which contains 1 to 10 carbon atoms. "Cyclic groups" are understood to include also heterocyclic groups, which may have one or two hetero atoms in the ring, which may be selected from a nitrogen atom, an oxygen atom and a sulfur atom. A methoxy group, an ethoxy group or an n- or iso-propoxy group or an iso- or t-butoxy, a 1'-methoxy-cyclopentoxy or a tetrahydropyranyloxy group are examples.

In the sense of the present application, the concept of $C_{1-10}$ or $C_{1-15}$ acyl or acyloxy group" is understood to be a group with 1 to 10 or 1 to 15 carbon atoms of the linear or branched alkane carboxylic acids, such as formic acid, acetic acid, propionic acid, butyric acid, iso-butyric acid, heptanoic acid or undecanoic acid.

Within the sense of the present application, the concept of a "$C_{6-15}$ aryl group" is understood to include a substituted or unsubstituted aryl group with 6 to 15 carbon atoms, such as a phenyl group, a substituted phenyl group, such as a halogenated phenyl group or a nitrophenyl group, or a naphthyl group.

Within the sense of the present application, the concept of a "$C_{4-15}$ aryloxy group" is understood to include a carbocyclic or heterocyclic group with 4 to 15 carbon atoms. Examples are a benzoyloxy group, a 1- or 2-naphthinyloxy group, a 2- or 3-furanyloxy group, a 2- or 3-thienyl group and a 2-, 3- or 4-pyridinyloxy group.

Within the sense of the present application, the concept of a "$C_{7-15}$ alkylaryl group" is understood to include an aryl group, which is substituted by an alkyl group, the two group together having 7 to 15 carbon atoms. The aryl group may have additional substituents, such as a halogen atom. Examples are a toluenyl group (methylphenyl group), a halogenated toluenyl group, an ethylphenyl group, a dimethylphenyl group or a trimethylphenyl group.

Within the sense of the present application, the concept of a "$C_{7-15}$ alkylaryloxy group" is understood to be a "$C_{7-15}$ aralkyl group", such as a 3- or a 4-methylphenyloxy group, which is extended by an oxygen atom.

Within the sense of the present application, the concept of a "$C_{7-15}$ aralkyl group" is understood to include an alkyl group, which is substituted by an aryl group, the two groups together having 7 to 15 carbon atoms. The aryl group may have further substituents, such as a halogen atom. Examples are a free or an aromatically substituted benzyl group, such as a benzyl group or a halogenated benzyl group.

Within the sense of the present application, the concept of "$C_{7-15}$ aralkyloxy group" is understood to include "$C_{7-15}$ aralkyl groups", which has been extended by an oxygen atom, such as a benzyloxy group.

Within the sense of the present invention, the concept of "halogen" comprises a fluorine, chlorine, bromine or iodine atom.

Within the sense of the present application, the concept of "pseudohalogen" comprises a [cyanate, rhodanide,] *cyanato, thiocyanato,* cyano, or [azide] *azido* group.

Within the sense of the present application, the concept of "perfluoroalkyl group" comprises a branched or linear fluoroalkyl group with 1 to 3 carbon atoms, such as a trifluoromethyl, pentafluoroethyl, heptafluoro-n-propyl or heptafluoro-i-propyl group.

$R_1$ represents preferably a hydroxy or acyloxy group, especially a hydroxy group, formyloxy group, acetyloxy group, propionyloxy group, n-butyryloxy group, i-butyryloxy group, heptanyloxy group or undecanyl group.

If $R_2$ represents a $—(CH_2)_nCH_2Y$ group, n preferably is 1 and Y preferably represents a fluorine atom, a cyano or rhodanide group. If $R_2$ is a $—(CH_2)_m—CH{=}CH(CH_2)_p—R_6$ group, m preferably is 1 and $R_6$ preferably represents a methyl or ethyl group or a methoxy or ethoxy group.

*If $R_2$ represents a $—(CH_2)_oC{\equiv}CR_7$ group, o preferably is 1 and $R_7$ preferably represents a fluorine atom, a methyl group, or an ethyl group.*

It is particularly preferred if $R_2$ represents a hydrogen atom or a $C_{1-6}$ alkyl group, especially a methyl or ethyl group.

$R_3$ preferably represents a $C_{1-4}$ alkyl group, especially a methyl group.

$R_4$ preferably represents a fluorine, chlorine or bromine atom or a trifluormethyl or hydroxy group.

$R_5$ preferably represents a methyl or ethyl group.

The most preferred compounds are the following:

1) 4-chloro-17β-hydroxy-14α,15α-methylene-androst-4-ene-3-one
2) 4-chloro-17α-hydroxy-14α,15α-methylene-androst-4-ene-3-one
3) 4-chloro-17β-hydroxy-14β,15β-methylene-androst-4-ene-3-one
4) 4-chloro-17α-hydroxy-14β,15β-methylene-androst-4-ene-3-one
5) 4-bromo-17β-hydroxy-14α,15α-methylene-androst-4-ene-3-one 6) 4-bromo-17α-hydroxy-14α,15α-methylene-androst-4-ene-3-one
7) 4-bromo-17β-hydroxy-14β,15β-methylene-androst-4-ene-3-one
8) 4-bromo-17α-hydroxy-14β,15β-methylene-androst-4-ene-3-one
9) 4-fluoro-17β-hydroxy-14α,15α-methylene-androst-4-ene-3-one
10) 4-fluoro-17α-hydroxy-14α,15α-methylene-androst-4-ene-3-one
11) 4-fluoro-17β-hydroxy-14β,15β-methylene-androst-4-ene-3-one
12) 4-fluoro-17α-hydroxy-14β,15β-methylene-androst-4-ene-3-one
13) 4,17β-dihydroxy-14α,15α-methylene-androst-4-ene-3-one
14) 4,17α-dihydroxy-14α,15α-methylene-androst-4-ene-3-one
15) 4,17β-dihydroxy-14β,15β-methylene-androst-4-ene-3-one
16) 4,17α-dihydroxy-14β,15β-methylene-androst-4-ene-3-one
17) 4-trifluoromethyl-17β-hydroxy-14α,15α-methylene-androst-4-ene-3-one
18) 4-trifluoromethyl-17α-hydroxy-14α,15α-methylene-androst-4-ene-3-one
19) 4-trifluoromethyl-17β-hydroxy-14β,15β-methylene-androst-4-ene-3-one
20) 4-trifluoromethyl-17α-hydroxy-14β,15β-methylene-androst-4-ene-3-one
21) 17β-hydroxy-14α,15α-methylene-androsta-1,4-diene-3-one
22) 17α-hydroxy-14α,15α-methylene-androsta-1,4-diene-3-one
23) 17β-hydroxy-14α,15α-methylene-androsta-1,4-diene-3-one
24) 17β-hydroxy-14β,15β-methylene-androsta-1,4-diene-3-one
25) 17α-hydroxy-14β,15β-methylene-androsta-1,4-diene-3-one
26) 4-chloro-17α-hydroxy-14α,15α-methylene-androsta-1,4-diene-3-one
27) 4-chloro-17β-hydroxy-14α,15α-methylene-androsta-1,4-diene-3-one
28) 4-chloro-17β-hydroxy-14β,15β-methylene-androsta-1,4-diene-3-one and
29) 4-chloro-17α-hydroxy-14β,15β-methylene-androsta-1,4-diene-3-one The inventive compounds and their pharmaceutically acceptable salts can be synthesized in that, in compounds of the general formula (II)

(II)

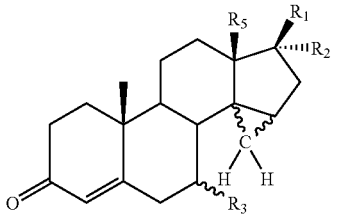

in which $R_1$, $R_2$, $R_3$, and $R_5$, which have the meanings given above, and there is an α or β cyclopropane group between C-14 and C-15, the 4,5 double bond is epoxidized under alkaline conditions with hydrogen peroxide and the resulting epoxide mixture is treated in a suitable solvent with acids of the general formula $HR_8$, in which $R_8$ may be a halogen atom or a pseudohalogen. Moreover, the corresponding 4-bromo compounds can also be synthesized by the addition of bromine by means of bromine, N-bromosuccinimide or N-bromoacetamide to compounds of the general formula (II) in a mixture of acetic acid and ether in the presence of a proton acceptor, such as collidine, (X. S. Fei et. al., J. Chem. Soc. Perkin Trans. 1, 1998, 1139–1142).

4-Hydroxy compounds are obtained by reacting the epoxide mixture above with catalytic amounts of mineral acid, such as sulfuric acid (P. S. Furth et. al. J. Enzyme Inhibition, 1990, Vol. 4, 131–135).

Compounds of the general formula (I) with an additional double bond in the 1,2 position can be obtained easily by methods known to those skilled in the art, such as the dehydrogenation of the 4-ene-3-one system by means of 2,3-dichloro-5,6-dicyanobenzoquinone in a suitable solvent, such as dioxane, toluene or t-butanol.

4-Trifluormethyl compound of the general formula (I) can be obtained by the reaction of the 4-bromo compounds of the general formula (I), which are mentioned above, with methyl 2,2-difluoro-2-(fluorosulfonyl)acetate in dimethylformamide the presence of CuI (X. S. Fei et. al., J. Chem. Soc., Perkin Trans. 1, 1998, 1139–1142). The starting compounds of formula (II) can be synthesized by known methods or by the method described in the German application with the application No. 198 27 523.4 (PCT/DE99/01794). The introduction of the groups, which are analogous to the groups $R_1$, $R_2$, $R_3$ and $R_5$ occurring there and are claimed here, is described in the protective right mentioned.

Pharmaceutical compositions for the oral, rectal, subcutaneous, intravenous or intramuscular applications, which contain at least one compound of the general formula (I) and/or their acid addition salts as active ingredient, together with the conventional vehicles and diluents are also an object of the present invention.

Pharmaceutical preparations of the invention are prepared with the usual solid or liquid vehicles and/or diluents and the inactive ingredients, the use of which is generally customary in accordance with the desired type of application, in a suitable dosage and by a known procedure. In the case of a preferred oral form of administration, preferably tablets, film-coated tablets, coated tablets, capsules, pills, powders, solutions or suspensions are prepared also in sustained release form. In addition, parenteral forms of medicinal drugs, such as injection solutions or suspensions, can also be considered.

Medicinal drug forms as tablets can be obtained for example by mixing the active ingredient with the known inert materials, such as dextrose, sugar, sorbitol, mannitol, polyvinylpyrrolidone, disintegrants such as corn starch or alginic acid, binders such as starch or gelatin, lubricants such as magnesium stearate or talc and/or agents, which can achieve a sustained release effect, such as carboxypolymethylene, carboxymethylcellulose, cellulose acetate phthalate or polyvinyl acetate. The tablets may also consist of several layers.

Similarly, coated tablets can be prepared by coating cores, prepared similarly to the tablets, with agents used in conventional tablet coatings, such as polyvinylpyrrolidone or shellac, gum arabic, talc, titanium dioxide or sugar. The tablet coating may consist of several layers, the inert materials, named above, for example being used.

To improve the taste, the solutions or suspensions with the inventive active ingredient can be mixed with materials such as saccharin, cyclamate or sugar and/or with aromatic and flavoring materials such as vanillin or orange extract.

Moreover, they may be mixed with suspending agents, such as sodium carboxymethylcellulose, or preservatives, such as p-hydroxybenzoic acid.

Capsules can be prepared by mixing medicinal drugs with vehicles, such as lactose or sorbitol, which are then brought into the capsules.

Suppositories are prepared preferably by mixing active ingredients with suitable vehicles, such as neutral fats or polyethylene glycols or their derivatives.

The pharmaceutical forms of preparations furthermore can be percutaneous forms, such as transdermal therapeutic systems (TTS) or gels, sprays or ointments or intranasal forms, such as nose sprays or oral nose drops.

The inventive 14,15-cyclopropanoandrostanes of the general formula (I) are compounds with hormonal (gestagenic and/or androgenic) activity.

For example, the compound of the general formula (I), in which $R_1$ is a hydroxyl group, $R_2$ and $R_3$ are hydrogen atoms, $R_5$ is a methyl group and X is a $CH_2$ group and the 14,15 cyclopropane ring is in the α position, namely 4-chloro-17β-hydroxy-14α,15α-methylene-androst-4-ene-3-one is an androgen.

The 4-chloro-17β-hydroxy-14α,15α-methylene-androst-4-ene-3-one binds to the extent of 42%±3% to the androgen receptor of the rat prostate (reference substance. 17β-hydroxy-17α-methyl-estra-4,9,11-triene-3-one; R 1881). On the other hand, there is practically no binding to the progesterone receptor of the rabbit uterus (reference substance: progesterone). It was possible to demonstrate distinct androgenic activity in the Hershberger test. On the other hand, there is hardly any gestagenic activity in the pregnancy maintenance test.

These test results open up various possibilities for the inventive compounds of the general formula (I) for fertility control in men, hormone replacement therapy (HRT) in men and women or the treatment of hormonally induced diseases in men and women, such as endometriosis, breast cancer or hypogonadism.

The following examples are intended to explain the invention in greater detail without limit it.

EXAMPLES

Example 1

17β-Hydroxy-4,5-epoxy-14α,15α-methylene-androstan-3-one

Synthesis of 4,5-Epoxides

17β-hydroxy-14α,15α-methylene-androst-4-ene-3-one (2 g) is dissolved in 80 mL of methanol and treated at 0° C. with 26 mL of a hydrogen peroxide solution (35%). While stirring, 5.2 mL of a 10% sodium hydroxide solution are added, the stirring being continued at 0° C. for 30 hours. The reaction solution is mixed with 50 mL of dichloromethane and 25 mL of water and the organic phase is removed, washed with semi-concentrated thiosulfate solution, dried and evaporated to dryness. The residue obtained consists of a mixture of 4α,5α- or 4β,5β-epoxides and is used in the subsequent step without further purification.

Example 2

17α-Hydroxy-4,5-epoxy-14α,15α-methylene-androstan-3-one

The compound, named above, can be obtained from 17α-hydroxy-14α,15α-methylene-androst-4-ene-3-one by a method, similar to that of Example 1.

Example 3

4-Chloro-17β-hydroxy-14α,15α-methylene-androst-4-ene-3-one

17β-hydroxy-4,5-epoxy-14α,15α-methylene-androstan-3-one (1.5 g) is dissolved in 150 mL of acetone and treated at 0° C. with 5.5 mL of concentrated hydrochloric acid. After 24 hours at 0° C., the reaction mixture is neutralized with sodium carbonate solution and the acetone is evaporated. The residue is extracted with dichloromethane. The organic extracts are dried and concentrated. After crystallization from ethanol, 4-chloro-17β-hydroxy-14α,15α-methylene-androst-4-ene-3-one is obtained.

$^1$H-NMR: 0.12 (1H, dd, I=5.5, 3.3 Hz, $CH_2$-bridge), 0.22 (1H, dd, J=8.2, 5.5 Hz, $CH_2$-bridge), 0.99 (3H, s, H-18), 1.30 (3H, s, H-19), 3.49 (1H, dd, J=9.3, 7.1 Hz, H-17).

Example 4

4-Chloro-17α-hydroxy-14α,15α-methylene-androst-4-ene-3-one

17α-Hydroxy-14α,15α-methylene-androst-4-ene-3-one is reacted by a method, similar to that of Example 3.

$^1$H-NMR: 0.32 (1H, dd, J=7.7, 4.9 Hz, $CH_2$-bridge), 0.72 (1H, dd, J=4.4, 3.3 Hz, $CH_2$-bridge), 0.99 (3H, s, H-18), 1.29 (3H, s, H-19), 3.80 (1H, d, J=6.0 Hz, H-17).

Example 5

4,17β-Dihydroxy-14α,15α-methylene-androst-4-ene-3-one

An epoxide mixture (3.5 g), 17β-hydroxy-4,5-epoxy-14α,15α-methylene-androstan-3-one, (step 1) is dissolved in 50 mL of acetic acid, which contains 2% by volume of concentrated sulfuric acid. The solution is allowed to stand for 3 days at 10° C. After that, it is treated with 200 mL ethyl acetate and neutralized with sodium carbonate solution. The organic phase is dried and concentrated. The residue is dissolved in 100 mL of methanol, treated with 4 g of potassium hydroxide, refluxed for 1 hour and then cooled. After neutralization with 50% acetic acid, it is poured into 1 L of water and the crystals are filtered off with suction, 4,17β-Dihydroxy-14α,15α-methylene-androst-4-ene-3-one being obtained.

$^1$H-NMR: 0.13 (1H, dd, J=5.6, 3.2 Hz, $CH_2$-bridge), 0.24 (1H, dd, J=8.3, 5.6 Hz, $CH_2$-bridge), 0.99 (3H, s, H-18), 1.30 (3H, s, H-19), 3.50 (1H, dd, J=9.4, 6.8 Hz, H-17), 6.10 (1H, s, 4-OH).

Example 6

4-Bromo-17β-hydroxy-14α,15α-methylene-androst-4-ene-3-one

The target compound is synthesized in a manner similar to the synthesis of 4-Chloro-17β-hydroxy-14α,15α-methylene-androst-4-ene-3-one, 48% hydrobromic acid being used instead of hydrochloric acid.

$^1$H-NMR: 0.12 (1H, dd, J=5.5, 3.3 Hz, $CH_2$-bridge), 0.21 (1H, dd, J=8.4, 5.4 Hz, $CH_2$-bridge), 1.00 (3H, s, H-18), 1.33 (3H, s, H-19), 3.49 (1H, dd, J=9.3, 7.1 Hz, H-17).

Example 7

4-Trifluoromethyl-17β-hydroxy-14α,15α-methylene-androst-4-ene-3-one

4-Bromo-17β-hydroxy-14α,15α-methylene-androst-4-ene-3-one (1.5 g) is dissolved in 180 mL of dimethylformamide and stirred at 75° C. for 12 hours with 1 g of CuI as well as 2.8 mL of methyl 2,2-difluoro-2-(fluorosulfonyl) acetate. After working up and chromatographic purification, 4-Trifluoromethyl-17β-hydroxy-14α,15α-methylene-androst-4-ene-3-one is obtained.

$^1$H-NMR: 0.14 (1H, dd, J=5.5, 3.0 Hz, $CH_2$-bridge), 0.25 (1H, dd, J=8.2, 5.8 Hz, $CH_2$-bridge), 1.00 (3H, s, H-18), 1.32 (3H, s, H-19), 3.51 (1H, m, H-17). $^{19}$F-NMR: −55.3 (3F, s, 4-$F_3$C).

Example 8

17β-Hydroxy-14α,15α-methylene-androsta-1,4-diene-3-one

17β-Hydroxy-14α,15α-methylene-androst-4-ene-3-one (4 g) in 160 mL of toluene is stirred for 6 days at 85° C. with 3.2 g of 2,3-dichloro-5-6-dicyanobenzoquinone. The precipitate is filtered off, washed with a little toluene and the filtrates and washings are evaporated to dryness. The residue is purified by chromatography, 17β-Hydroxy-14α,15α-methylene-androsta-1,4-diene-3-one being obtained.

$^1$H-NMR: 0.13 (1H, dd, J=5.6, 3.2 Hz, $CH_2$-bridge), 0.24 (1H, dd, J=8.3, 5.6 Hz, $CH_2$-bridge), 0.98 (3H, s, H-18), 1.35 (3H, s, H-19), 3.50 (1H, m, H-17), 6.06 (1H, m, H-4); 6.22 (1H, dd, J=12.09; 1.65 Hz, H{2}), 7.04 (1H, d, J=9.9 Hz, H-1).

Example 9

4-Chloro-17β-hydroxy-14α,15α-methylene-androsta-1,4-diene-3-one

This compound is prepared from 4-chloro-17β-hydroxy-14α,15α-methylene-androst-4-ene-3-one by a method to that of Example 6.

$^1$H-NMR: 0.13 (1d, dd, j=5.6, 3.2 Hz, $CH_2$-bridge), 0.24 (1H, dd, J=8.3, 5.6 Hz, $CH_2$-bridge), 0.98 (3H, s, H-18), 1.35 (3H, s, H-19), 3.50 (1H, m, H-17), 6.22 (1H, dd, j=12.09, 1.65 Hz, H{2}), 7.04 (1H, d, J=9.9 Hz, H-1).

What is claimed is:

1. Unsaturated [14,15-cyclopranoandrostanes] *14,15-cyclopropanoandrostanes* of [the] formula (I):

(I)

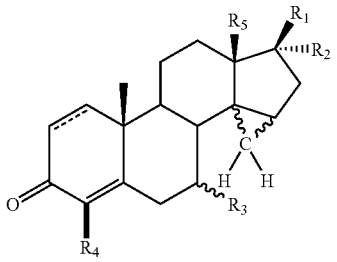

wherein $R_1$ [is] *represents* a hydrogen atom, a hydroxy group, a $C_{1-10}$-alkyl *group*, a $C_{1-10}$-alkyloxy *group*, a $C_{1-15}$ acyloxy *group*, a $C_{4-15}$-aryloxy *group*, a $C_{7-15}$-aralkyloxy *group*, or a $C_{7-15}$-alkylaryloxy group;

$R_2$ represents a hydrogen atom, a hydroxy group, a $C_{1-10}$ alkyl group, a $C_{1-10}$ acyl group, a $C_{1-10}$ acyloxy group, a $C_{6-15}$ aryl group, a $C_{7-15}$ aralkyl group, a $C_{7-15}$ alkylaryl group, a $—(CH_2)_nCH_2Y$ group in which n=0, 1 or 2 and Y represents a halogen atom[or a pseudohalogen], *a cyano group, an azido group, a cyanato group, or a thiocyanato group*; *a* $—(CH_2)_m CH{=}CH(CH_2)_pR_6$ *group* in which m=0, 1, 2, or 3 and p=0, 1, or 2 and $R_6$ represents a hydrogen atom, a $C_{1-10}$-alkyl group, a $C_{6-15}$ aryl group, a $C_{7-15}$ aralkyl group, a $C_{7-15}$ alkylaryl group, a hydroxyl group, a $C_{1-10}$ alkyloxy group, or a $C_{1-10}$ acyloxy group; *a* $—(CH_2)_oC{\equiv}CR_7$ *group* in which o=0, 1, or 2 and $R_7$ represents a hydrogen atom, a halogen atom, a $C_{1-10}$ alkyl group, a $C_{6-15}$ aryl group, a $C_{7-15}$ aralkyl group, a $C_{7-15}$ alkylaryl group, or a $C_{1-10}$ acyl group; or $R_1$ and $R_2$ together represent a keto group, a methylene group, a difluoromethylene group or, with inclusion of C-17, a spirooxirane or a 2,2-dimethyl-1,3-dioxolane; [ in which optionally a 1,2 double bond is present;]

$R_3$ represents a hydrogen atom, 1 [or] a α-$C_{1-10}$ alkyl group, or a β-$C_{1-10}$ alkyl group;

$R_4$ represents a halogen atom, a [pseudohalogen] *cyano group, an azido group, a thiocyanato group, a cyanato group,* a hydroxy group, or a perfluoroalkyl group;

$R_5$ represents a $C_{1-4}$ alkyl group;

[in which] an α-cyclopropane group or a β-cyclopropane group is *present* between C-14 and C-15;

*in which optionally a 1,2-double bond is present and* with the proviso that, if said 1,2-double bond is present, then $R_4$ can [be] *represent* a hydrogen atom in addition to said halogen atom, said [pseudohalogen] *cyano group, said azido group, said thiocyanato group,* said hydroxy group, or said perfluoroalkyl group;

or pharmaceutically tolerated salts thereof.

2. The unsaturated [14,15-cyclopranoandrostanes] *14,15-cyclopropanoandrostanes* as defined in claim 1, wherein Y [is] *denotes* a fluorine atom, a chlorine atom, a bromine atom, an iodine atom, a cyano group, an [azide] *azido* group, or a [rhodanide] *thiocyanato* group.

3. The unsaturated [14,15-cyclopranoandrostanes]*14,15-cyclopropanoandrostanes* as defined in claim 1, wherein $R_7$ [is] *denotes* a fluorine atom, a chlorine atom, a bromine atom, or an iodine atom.

4. The unsaturated [14,15-cyclopranoandrostanes] *14,15-cyclopropanoandrostanes* as defined in claim 1, wherein $R_4$ [is] *denotes* a fluorine atom, a chlorine atom, a bromine atom, an [azide] *azido* group, or a [rhodanide] *thiocyanato* group.

5. The unsaturated [14,15-cyclopranoandrostanes] *14,15-cyclopropanoandrostanes* as defined in claim 1, wherein $R_1$ [is] *denotes* a hydroxy group or an acyloxy group.

6. The unsaturated [14,15-cyclopranoandrostanes] *14,15-cyclopropanoandrostanes* as defined in claim 5, wherein said acyloxy group is a formyloxy, an acetyloxy, a propionyloxy, a n-butyryloxy, an isobutyryloxy, a heptanyloxy, or an undecanyloxy group.

7. The unsaturated [14,15-cyclopranoandrostanes] *14,15-cyclopropanoandrostanes* as defined in claim 1, wherein $R_2$ is a hydrogen atom or an alkyl group.

8. The unsaturated [14,15-cyclopranoandrostanes] *14,15-cyclopropanoandrostanes* as defined in claim 7, wherein said alkyl group is a methyl group or an ethyl group.

9. The unsaturated [14,15-cyclopranoandrostanes] *14,15-cyclopropanoandrostanes* as defined in claim 1, wherein $R_3$ is a methyl group.

10. The unsaturated [14,15-cyclopranoandrostanes] *14,15-cyclopropanoandrostanes* as defined in claim 1, wherein $R_4$ [is] *denotes* a fluorine atom, a chlorine atom, a bromine atom, a hydroxy group, or a trifluoromethyl group.

11. The unsaturated [14,15-cyclopranoandrostanes] *14,15-cyclopropanoandrostanes* as defined in claim 1, wherein $R_5$ [is] *denotes* a methyl group or an ethyl group.

12. The unsaturated [14,15-cyclopranoandrostanes] *14,15-cyclopropanoandrostanes* selected from the group consisting of 4-chloro-17β-hydroxy-14α,15α-methylene-androst-4-ene-3-one,
4-chloro-17α-hydroxy-14α,15α-methylene-androst-4-ene-3-one,
4-chloro-17β-hydroxy-14β,15β-methylene-androst-4-ene-3-one,
4-chloro-17α-hydroxy-14β,15β-methylene-androst-4-ene-3-one,
4-bromo-17β-hydroxy-14α,15α-methylene-androst-4-ene-3-one,
4-bromo-17α-hydroxy-14α,15α-methylene-androst-4-ene-3-one,
4-bromo-17β-hydroxy-14β,15β-methylene-androst-4-ene-3-one,
4-bromo-17α-hydroxy-14β,15β-methylene-androst-4-ene-3-one,
4-fluoro-17β-hydroxy-14α,15α-methylene-androst-4-ene-3-one,
4-fluoro-17α-hydroxy-14α,15α-methylene-androst-4-ene-3-one,
4-fluoro-17β-hydroxy-14β,15β-methylene-androst-4-ene-3-one,
4-fluoro-17α-hydroxy-14β,15β-methylene-androst-4-ene-3-one,
4,17β-dihydroxy-14α,15α-methylene-androst-4-ene-3-one,
4,17α-dihydroxy-14α,15α-methylene-androst-4-ene-3-one,
4,17β-dihydroxy-14β,15β-methylene-androst-4-ene-3-one,
4,17α-dihydroxy-14β,15β-methylene-androst-4-ene-3-one,
4-trifluoromethyl-17β-hydroxy-14α,15α-methylene-androst-4-ene-3-one,
4-trifluoromethyl-17α-hydroxy-14α,15α-methylene-androst-4-ene-3-one,
4-trifluoromethyl-17β-hydroxy-14β,15β-methylene-androst-4-ene-3-one,
4-trifluoromethyl-17α-hydroxy-14β,15β-methylene-androst-4-ene-3-one,
17β-hydroxy-14α,15α-methylene-androsta-1,4-diene-3-one,
17α-hydroxy-14α,15α-methylene-androsta-1,4-diene-3-one,
17β-hydroxy-14β,15β-methylene-androsta-1,4-diene-3-one,
17α-hydroxy-14β,15β-methylene-androsta-1,4-diene-3-one,
4-chloro-17α-hydroxy-14α,15α-methylene-androsta-1,4-diene-3-one,
4-chloro-17β-hydroxy-14α,15α-methylene-androsta-1,4-diene-3-one,
4-chloro-17β-hydroxy-14β,15β-methylene-androsta-1,4-diene-3-one, and
4-chloro-17α-hydroxy-14β,15β-methylene-androsta-1,4-diene-3-one.

13. A method [for the] *of* synthesis of the [14,15-cyclopranoandrostanes] *14,15-cyclopropanoandrostanes* defined in claim 1, wherein, in compounds of formula (II):

(II)

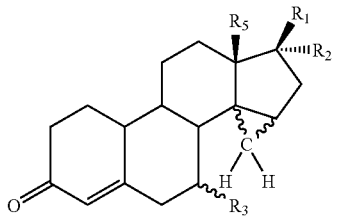

in which $R_1$, $R_2$, $R_3$, $R_5$ are as defined in claim 1[, 4,5 double] *and in which a 4,5-double bond is present, the 4,5-double* bond is epoxidized with hydrogen peroxide under alkaline conditions and the resulting epoxide mixture is treated in a solvent with acids of [the] formula $HR_8$, $R_8$ being a halogen atom, *a cyano group, an azido group, a cyanato,* or a [pseudohalogen atom,] *thiocyanato group,* or reacted with catalytic amounts of a mineral acid[,] to obtain 4-bromo -compounds and, optionally, the obtained 4-bromo compounds of the formula (I), as defined in claim 1, are reacted with methyl 2,2-difluoro-2-(fluorosulfonyl) acetate in dimethylformamide in the presence of CuI.

14. The method as defined in claim 13, wherein said halogen atom [is] *denotes* a fluorine, chlorine, or bromine atom.

15. The method as defined in claim 13, wherein [said pseudohalogen is an azide or a rhodanide] $R_8$ *represents said azido or said thiocyanato* group.

16. A pharmaceutical composition containing at least one of the unsaturated [14,15-cyclo-pranoandrostanes] *14,15-cyclopropanoandrostanes* defined in claim 1 and at least one additional ingredient selected from the group consisting of pharmaceutically tolerated inactive materials and vehicles.

17. A method of hormone replacement therapy in a man or woman in need of said therapy, said method comprising administering to said man or said woman an effective amount of at least one of the unsaturated [14,15-cyclopranoandrostanes] *14,15-cyclopropanoandrostanes* as defined in claim 1 for said hormone replacement therapy.

18. A method of controlling fertility of a human being, said method comprising administering to said human being an effective amount of at least one of the unsaturated [14,15-cyclopranoandrostanes] *14,15-cyclopropanoandrostanes* as defined in claim 1 for controlling said fertility.

19. A method of treating a hormone-induced disease suffered by a man or a woman, said method comprising administering to said man or said woman an effective amount of at least one of the unsaturated [14,15-cyclopranoandrostanes] *14,15-cyclopropanoandrostanes* as defined in claim 1 for treating said hormone-induced disease.

20. The method as defined in claim 19, wherein said hormone-induced disease is endometriosis, breast cancer, or hypogonadism.

* * * * *